United States Patent
Stabile et al.

(10) Patent No.: US 9,688,658 B1
(45) Date of Patent: Jun. 27, 2017

(54) PROCESS FOR THE OPTICAL PURIFICATION OF ESOMEPRAZOLE

(71) Applicant: F.I.S.—FABBRICA ITALIANA SINTETICI S.P.A., Montecchio Maggiore (VI) (IT)

(72) Inventors: Paolo Stabile, Verona (IT); Diego Rasia, Trissino (IT); Nicola Faccin, Valdagno (IT); Moreno Bertolazzi, Costalunga (IT)

(73) Assignee: F.I.S.—FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 15/501,329

(22) PCT Filed: Feb. 23, 2016

(86) PCT No.: PCT/EP2016/053710
§ 371 (c)(1),
(2) Date: Feb. 2, 2017

(87) PCT Pub. No.: WO2016/142165
PCT Pub. Date: Sep. 15, 2016

(30) Foreign Application Priority Data

Mar. 6, 2015 (EP) .................................... 15157974

(51) Int. Cl.
C07D 401/12 (2006.01)

(52) U.S. Cl.
CPC ........ *C07D 401/12* (2013.01); *C07B 2200/07* (2013.01)

(58) Field of Classification Search
CPC ..................................................... C07D 401/12
USPC ....................................................... 546/273.7
See application file for complete search history.

(56) References Cited

FOREIGN PATENT DOCUMENTS

WO    9702261 A1    1/1997

OTHER PUBLICATIONS

Hein et al., "Resolution of Omeprazole Using Coupled Preferential Crystallization: Efficient Separation of a Nonracemizable Conglomerate Salt under Near-Equilibrium Conditions", Organic Process Research & Development, 2013, vol. 17, No. 6, pp. 946-950.
Song et al., "Catalytic Asymmetric Synthesis of Esomeprazole by a Titanium Complex with a Hexa-aza-triphenolic Macrocycle Ligand", Synthetic Communications, 2014, vol. 45, No. 1, pp. 70-77.
International Search Report and Written Opinion for International Application No. PCT/EP2016/053710 (10 Pages) (Mar. 30, 2016).

*Primary Examiner* — Patricia L Morris
(74) *Attorney, Agent, or Firm* — Lucas & Mercanti, LLP

(57) ABSTRACT

An efficient process for increasing the optical purity of the active pharmaceutical ingredient Esomeprazole, by means of a substantially quantitative and selective precipitation and removal of Omeprazole is provided.

15 Claims, No Drawings

PROCESS FOR THE OPTICAL PURIFICATION OF ESOMEPRAZOLE

CROSS-REFERENCE TO RELATED APPLICATIONS

This application is a 371 of PCT/EP2016/053710, filed Feb. 23, 2016, which claims the benefit of European Patent Application No. 15157974.5, filed Mar. 6, 2015.

TECHNICAL FIELD

Object of the present invention is an efficient process for increasing the optical purity of the active pharmaceutical ingredient Esomeprazole.

STATE OF THE ART

Esomeprazole is the (S)-enantiomer of the racemic compound and active pharmaceutical ingredient named Omeprazole and, as Omeprazole, is itself an active ingredient classified as proton pump inhibitor.

Esomeprazole is thus also named (S)-(−)-Omeprazole or simply (S)-Omeprazole.

Esomeprazole has the following structural chemical formula (I):

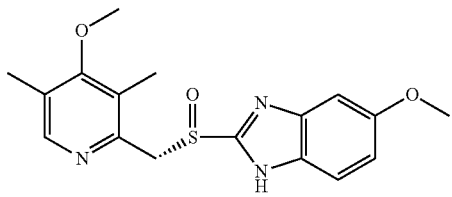

(I)

wherein the sulfur atom is the asymmetric center that provides chirality to the molecule, i.e. the chiral center is on the sulfur atom.

Omeprazole, a compound consisting of a racemic mixture of the enantiomers (S)-Omeprazole (i.e. Esomeprazole) and (R)-Omeprazole, has the following structural formula (III):

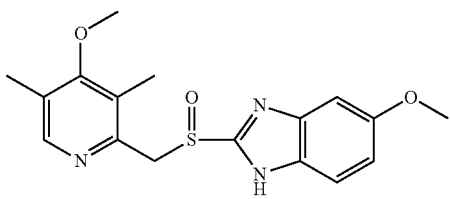

(III)

wherein (S)-Omeprazole and (R)-Omeprazole have respectively the following chemical structures (I) and (II):

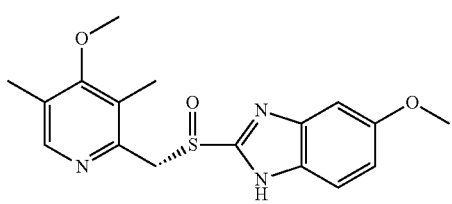

(I)

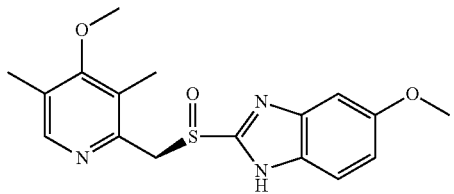

(II)

Other active pharmaceutical ingredients (abbreviated APIs) belonging to the same therapeutic category and to the family of the "Prazoles" are, for example, the following: Lansoprazole, Dexlansoprazole, Pantoprazole, Rabeprazole, Picoprazole, Iraprazole, etc.

All the aforementioned active substances act limiting acid gastric secretion.

Esomeprazole currently present on the market is characterized by specific solid forms which are Esomeprazole Magnesium trihydrate having stoichiometry (2:1:3) and Esomeprazole sodium salt (1:1).

Esomeprazole is characterized by an 1H-benzimidazole heterocyclic system, by a (pyridin-2-yl)methyl group and by an optically active sulphoxyde group, in particular, having S configuration and providing negative optical rotation.

Said chemical groups constitute the skeleton of all the active pharmaceutical ingredients belonging to the family of Prazoles which therefore differ each other in the substituents of both the aromatic systems and for the sulphoxyde group which can be or not optically active.

Chemical names that define Esomeprazole are 1H-Benzimidazole, 5-methoxy-2-[(S)-[(4-methoxy-3,5-dimethyl-2-pyridinyl)methyl]sulfinyl]- or 5-methoxy-2-[(S)-[(4-methoxy-3,5-dimethyl-2-pyridinyl)methyl]sulfinyl]-1H-benzimidazole.

A known process for the synthesis of Esomeprazole is disclosed in the application EP652872 and comprises the separation of diasteromeric derivatives of Omeprazole, separated by means of chromatography or by fractional crystallization. The efficiency of said process is intrinsically very limited.

The process disclosed in WO9602535 is based on an efficient enantioselective oxidation of prochiral heterocyclic sulfide carried out by means of chiral complexes of titanium and in presence of a base. The typical conditions of the process imply the use of titanium isopropoxyde, L-(+)-diethyltartrate and cumene hydroperoxide. This process provides enriched mixtures of optical isomers of Omeprazole having ratio of (S)-Omeprazole to (R)-Omeprazole higher than 90:10 (weight/weight).

In the recent years a new technology for the preparation of Esomeprazole has been developed with the aim of preparing Esomeprazole at low industrial costs. Said technology is based on the optical resolution of Omeprazole mediated by chiral hosts, such as for example L-(+)-diethyltartrate as disclosed in WO2006040635 or other chiral ligands.

In particular, the optical resolution of the racemic compound Omeprazole is carried out by means of the formation and isolation of Esomeprazole (S)-(−)-BINOL complex, also named Esomeprazole (S)-BINOL complex, having the following formula:

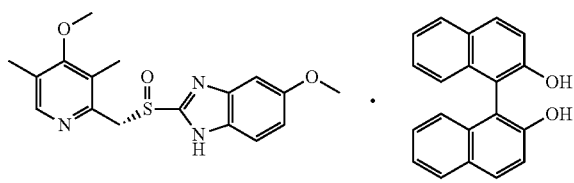

It is well known and described in the literature that Esomeprazole (S)-(−)-BINOL complex is an inclusion complex which can be well suitable as a key intermediate for the preparation of Esomeprazole and salts thereof, such as, for example, Esomeprazole Magnesium trihydrate or Esomeprazole sodium.

The synthesis of Esomeprazole (S)-(−)-BINOL complex by reaction of Omeprazole with (S)-(−)-BINOL followed by the isolation of this complex as solid, allows the separation of the S isomer, i.e. Esomeprazole, from the other isomer, (R)-Omeprazole, which remains in the mother liquors.

It is already part of the state of the art the preparation of Esomeprazole (S)-(−)-BINOL complex from racemic mixtures of (S)-Omeprazole and (R)-Omeprazole (i.e. from Omeprazole), or also from enriched mixtures of (S)-Omeprazole and (R)-Omeprazole, said enriched mixtures being enriched in (S)-Omeprazole, wherein said mixtures are prepared for example through the enantioselective oxidation disclosed in WO9602535.

Nevertheless, most of the known processes for the synthesis of Esomeprazole through the preparation of Esomeprazole (S)-(−)-BINOL complex are affected by the problem of the relatively low chemical purity of the product, therefore said procedures are followed by re-crystallization and/or purification of the product.

Moreover, the use of the chiral agent (S)-(−)-BINOL to resolve Omeprazole or to increase the optical purity of Esomeprazole has the intrinsic drawback related to the poor molar yield and to the industrial cost of said resolving agent.

A competitive method, in terms of cost, to increase the optical purity of a chiral compound or, in other words, to increase the enantiomeric purity of a chiral compound, consists in the removal of the racemic compound wherein said removal is based on the concept that an enantiomer has different solubility in comparison to the racemic compound, racemic compound which is therefore an impurity of the pure enantiomer compound.

The method of increasing the optical purity of an optically active compound through the removal of the racemic compound is well known in the chemical and/or pharmaceutical field. A representative example of said technology is disclosed in the patent publication FR2863609.

Said technology has been also successfully applied for the optical purification of Prazoles APIs and also for the purification of Esomeprazole.

The publication WO97/02261 indeed discloses the enhancement of optical purity of enriched mixtures of (R)-Omeprazole (examples 1-3) and (S)-Omeprazole, i.e. Esomeprazole (examples 4-7), by means of precipitation and filtration of the racemate (Omeprazole) from solutions containing said optically enriched mixtures in solvents such as acetonitrile, 2-butanone, acetone, ethyl acetate, ethanol and toluene.

Examples from 8 to 9 of WO97/02261 show how said process for increasing the optical purity of (R)-Omeprazole or Esomeprazole can be applied as the following step after the preparation of optically enriched mixtures of said compounds by means of asymmetric oxidation synthesis.

In particular, example 9 describes the preparation on kilo-lab scale of Esomeprazole having 95% of enatiomeric excess (e.e.) by means of asymmetric oxidation followed by removal of the racemate impurity Omeprazole by precipitation and filtration from a solution of acetone. In this case, the removal of the Omeprazole has brought to an increase of optical purity from 80% (e.e.) to 95% (e.e.).

Similar results were achieved in example 8 for the purification, on kilo-Lab scale, of the enantiomer (R)-Omeprazole, by precipitation and removal of Omeprazole, thus increasing the optical purity from 72.9% to 96.3% (e.e.).

In both said kilo-lab examples acetone was selected as the favorite solvent to carry out the removal of the racemate Omeprazole.

Finally, example 12, teaches that repeating the optical purification process other two times, it is possible to achieve optical purity, of another chemical derivative having formula (+)-(Ib), until the level of 99.6% (e.e.).

Although the procedures described in WO97/02261, especially those disclosed in examples 8 and 9, appear very easy and interesting by an economical point of view for increasing the optical purity of Esomeprazole, by the other side, the teaching described in WO97/02261 does not allow the preparation one-shot of Esomeprazole having high optical purity.

Indeed, the repetition of the purification process many times to achieve a higher level of optical purity is time consuming and impacts strongly on the cycle time of the process. Moreover, it is not described and said if, applying the teaching of example 12 to the Esomeprazole, for example to Esomeprazole as prepared in example 9, Esomeprazole having optical purity of 99.8% (e.e.) can be achieved or not, since example 12 is carried out on another different compound.

The process disclosed in WO97/02261 suffers therefore of relatively low efficiency so that, to achieve the pharmacopoeia standards and requirements in terms of optical purity, it needs to be re-applied many times.

However, it is not clear if applying all the teaching of WO97/02261, thus also including the repetition many times of the optical purification process, can be or not prepared Esomeprazole having high optical purity, for example Esomeprazole having optical purity of 99.6% (e.e.).

SUMMARY OF INVENTION

The problem addressed by the present invention is therefore that of providing an improved process, i.e. a more efficient process, which allows the preparation of Esomeprazole having high optical purity.

This problem is solved by a process as outlined in the annexed claims, whose definitions are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a process for the preparation of Esomeprazole having high optical purity of formula (I):

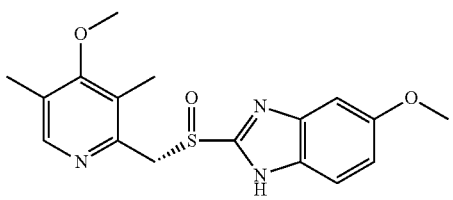

comprising the following steps:

A. providing a solution containing an enantiomerically enriched mixture of the optical isomers of formula (I) and (II):

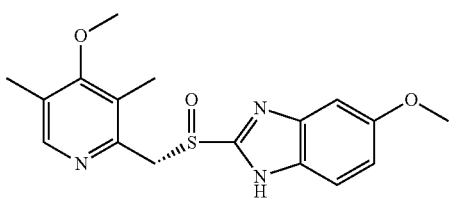

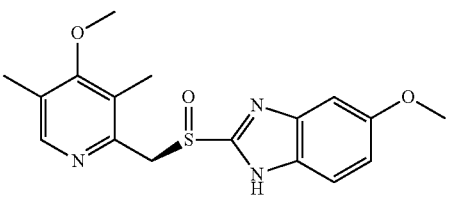

wherein the ratio between the optical isomers (I) and (II) is from 60:40 to 99:1, and wherein the solvent of said solution is dichloromethane;

B. promoting the crystallization of the compound of formula (III):

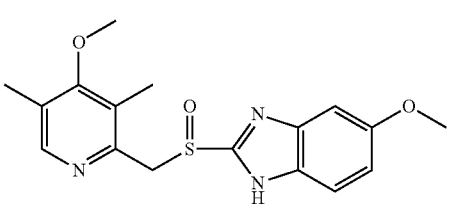

said compound being substantially in racemic form.

C. adding an ethereal solvent to the suspension prepared in the step B;

D. filtering the suspension prepared in the step C to remove the compound of formula (III);

E. isolating Esomeprazole having increased optical purity or salts thereof from the filtrated solution of the step D.

It has been indeed surprisingly found that it is possible to prepare Esomeprazole having a high optical purity, i.e. having a high enatiomeric excess, by addition of an ethereal solvent to a dichloromethane solution containing an enantiomerically enriched mixture of the optical isomers of formula (I) and (II):

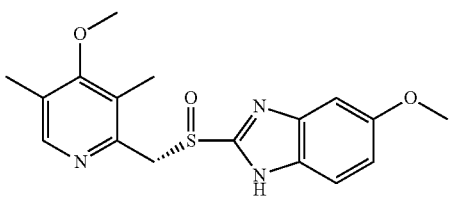

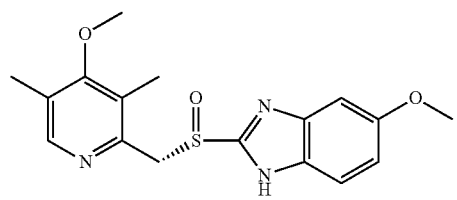

wherein the ratio between the optical isomers (I) and (II) is from 60:40 to 99:1, expressed as HPLC A/A %.

The addition of the ethereal solvent provides indeed the almost quantitative precipitation of the racemic Omeprazole, so that, substantially all the amount of the (R)-Omeprazole impurity is precipitated and then removed. As consequence of this effect, the increase of optical purity of Esomeprazole is dramatic, going for example from 60% (e.e.) to 99.7% (e.e.) in one step, only.

Furthermore, as additional effect, the addition of the ethereal solvent provides the selective precipitation of racemic Omeprazole, thus taking in solution, substantially quantitatively the Esomeprazole, thus providing the best possible yields in terms of purified product.

In other words, the extremely high efficiency in terms of increasing of optical purity provided by the process of the present invention is due to the effect of almost complete or quantitative precipitation of Omeprazole, therefore, to the substantially complete removal of (R)-Omeprazole.

Furthermore, the precipitation of Omeprazole is selective, since Omeprazole is almost quantitatively precipitated and, in the meantime, the main component Esomeprazole remains almost quantitatively solubilized in the organic phase.

It is believed that these effects of substantially quantitative precipitation and selective precipitation of Omeprazole are related to the particular combination of solvents being dichloromethane with the ethereal solvents.

The solvent dichloromethane is also named methylene chloride.

The process of the present invention, at the end of the step D., thus provides Esomeprazole having high optical purity, i.e. Esomeprazole having typically an optical purity higher than 99.0% (e.e.), i.e. higher than 99.5% expressed as HPLC A/A %.

Preferably, the process of the present invention provides Esomeprazole having high optical purity, i.e. Esomeprazole having typically an optical purity higher than 99.4% (e.e.), i.e. higher than 99.7% HPLC A/A %.

Obviously and optionally, the process of the present invention can be re-applied on the already optically purified Esomeprazole so that Esomeprazole having optical purity of 100% can be prepared.

However, at the end of the step E., typically the process of the present invention provides isolated Esomeprazole or salts thereof such as Esomeprazole Magnesium dihydrate, Esomeprazole Magnesium trihydrate or Esomeprazole sodium, wherein the content of the (R)-Omeprazole is not detected, i.e. Esomeprazole having optical purity of 100% (HPLC A/A %).

The step A. consists in providing a solution containing an enantiomerically enriched mixture of the optical isomers of formula (I) and (II):

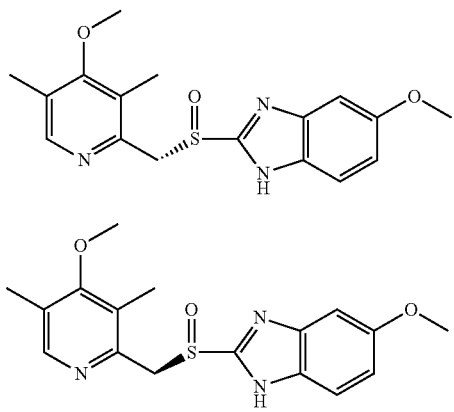

wherein the ratio between the optical isomers (I) and (II) is from 60:40 to 99:1. Said solution thus consists in an enantiomerically enriched mixture of the optical isomers of formula (I) and (II) dissolved in dichloromethane.

For preparing the solution of the step A. an enantiomerically enriched mixture of the optical isomers of formula (I) and (II) can be solubilized in dichloromethane or, alternatively and preferably, can be obtained at the end of the synthetic preparation of the molecule Esomeprazole, therefore, after a chemical reaction or during the work-up of the reaction mixture.

Preferably, the solution containing an enantiomerically enriched mixture of the optical isomers of formula (I) and (II) can be prepared during the work-up of the reaction mixture prepared by asymmetric oxidation of the synthetic precursor Ufiprazole having the following structure:

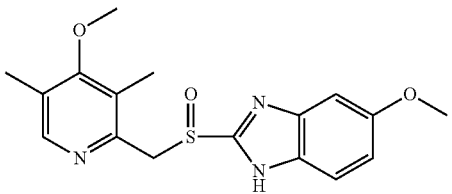

The ratio between the optical isomers (I) and (II) from 60:40 to 99:1, is intended as ratio weight by weight which, however, corresponds to the amount determined by HPLC A/A %, e.g. with the method of example 13, since the two enantiomers of formula (I) and (II) provide the same answer to the HPLC detector.

Expressed in terms of enatiomeric excess, the ratio between the optical isomers (I) and (II) from 60:40 to 99:1, means from 20% (e.e.) to 98% (e.e.).

According to a preferred embodiment of the present invention, in the step A., the ratio between the optical isomers (I) and (II) is from 75:25 to 85:15 since this ratio of isomers is that typically achieved by an asymmetric oxidation process of Ufiprazole.

According to a more preferred embodiment of the present invention, in the step A., the ratio between the optical isomers (I) and (II) is about 80:20.

The amount of dichloromethane for step A. ranges from 0.5 to 50 volumes compared with the mixture of optical isomers of formula (I) and (II).

The measure in volumes means unit of volume of solvent per unit, by weight, of the mixture of optical isomers (I) and (II). Thus, for example, 1 volume is 1 liter of solvent per 1 Kg of mixture of optical isomers (I) and (II) or 1 ml per 1 g or 1 microliter for 1 mg or 1 cubic meter for 1 ton of substance.

According to a preferred embodiment of the invention, the amount of dichloromethane for step A. ranges from 0.8 to 20 volumes compared with the mixture of optical isomers of formula (I) and (II).

According to a more preferred embodiment of the invention, the amount of dichloromethane for step A. ranges from 1 to 5 volumes compared with the mixture of optical isomers of formula (I) and (II), again more preferably from 1.5 to 2.0 volumes, the best being about 1.8 volumes.

The step B. of the process of the present invention consists in promoting the crystallization of the compound of formula (III):

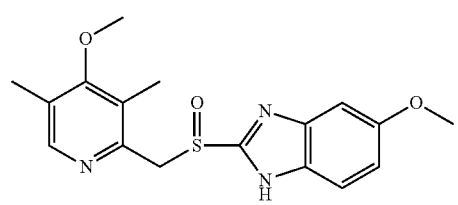

wherein said compound is substantially in racemic form.

The crystallization or precipitation of the compound of formula (III) provides the compound of formula (III) as a solid, and said solid is suspended in the organic solvent.

Thus, in step B., a suspension of the compound of formula (III) in dichloromethane is generated.

The solid compound of formula (III) is substantially in racemic form, i.e. is substantially Omeprazole, since it contains from 48.0% to 49.5% (HPLC A/A %) of the unwanted impurity (R)-Omeprazole, the rest being (S)-Omeprazole.

The amount from 48.0% to 49.5% (HPLC A/A %) of the unwanted impurity (R)-Omeprazole confirms that the precipitated solid compound of formula (III) is Omeprazole, containing, as an impurity thereof, a little amount of the product Esomeprazole ranging from 4% to 1% (HPLC A/A %). These data confirm the selectivity of the process in precipitating almost exclusively the Omeprazole, and leaving almost quantitatively in solution the product Esomeprazole, with a great benefit for the yield of the process.

In the step B., for promoting the crystallization or precipitation of the compound of formula (III) various methods are available, for example by concentration of the dichloromethane solution and/or by cooling down said solution and/or by seeding said solution with a seed of Omeprazole.

According to a preferred embodiment of the invention the crystallization or precipitation of the compound of formula (III) is carried out by concentration of the dichloromethane solution.

According to a preferred embodiment of the invention, the step B. of crystallization or precipitation of the compound of formula (III) is carried out by concentration of the dichloromethane solution of the step A., from a range from 20 to 3 volumes to a range from 5 to 1 volumes compared with the mixture of optical isomers (I) and (II).

According to a more preferred embodiment of the invention the crystallization or precipitation of the compound of formula (III) is carried out by concentration of the dichloromethane solution of the step A., from a range from 6 to 4 volumes to a range from 2.0 to 1.5 volumes compared with the mixture of optical isomers (I) and (II), more preferably from about 5.4 volumes to about 1.8 volumes.

The step C. of the process of the present invention is carried out by adding an ethereal solvent to the suspension of the compound of formula (III) in dichloromethane prepared in the step B;

According to a more preferred embodiment of the invention, the ethereal solvent containing from 5 to 10 atoms of carbon can be linear or cyclic, and can be for example, methyl-t-buthylether (abbreviated MTBE), diisopropylether (IPE), methylisobuthylether, dibuthylether (DBE), cyclopentyl methyl ether (CPME), methyl-tetrahydrofurane, diisobuthyether, n-buthylmethylether, pentylmethylether, tert-amylmethylether, etc.

According to an again more preferred embodiment of the invention the ethereal solvent is chosen in the group of methyl-t-buthylether, diisopropylether, dibuthylether, cyclopentyl methyl ether.

According to an again more preferred embodiment of the invention the ethereal solvent is methyl-t-buthylether.

The amount of ethereal solvent added in the step C. is typically comprised between 0.5 to 20 volumes compared with the mixture of optical isomers of formula (I) and (II).

According to a preferred embodiment of the invention, in the step C. is added an amount of the ethereal solvent comprised between 1 and 5 volumes compared with the mixture of optical isomers of formula (I) and (II), more preferably between 1.5 and 2.0, being about 1.8 volumes the best amount.

In the step C., the addition of the ethereal solvent to the suspension of the compound of formula (III) in dichloromethane is carried out one-pot or, preferably in a time comprised between 1 and 60 minutes, more preferably, the addition is performed in a time comprised between 20 and 40 minutes, being more preferred a time of about 30 minutes. Carrying out the addition in a time comprised between 1 and 60 minutes, better results are achieved in terms of optical purity of the final product. The addition of the ethereal solvent in a time comprised between 20 and 40 minutes provides better results since this slow addition allows for a more quantitative and a more selective precipitation of the Omeprazole of formula (III), without incorporating the Esomeprazole into the crystal, thus avoiding losses of product.

According to a preferred embodiment of the invention, in the step B. the crystallization or precipitation of the compound of formula (III) is carried out from a solution of from 3 to 20 volumes of dichloromethane and, in the step C., are added from 0.5 to 20 volumes of the ethereal solvent, both compared with the mixture of optical isomers of formula (I) and (II).

According to a more preferred embodiment of the invention, in the step B. the crystallization or precipitation of the compound of formula (III) is carried out from a solution of from 1 to 5 volumes of dichloromethane and, in the step C., are added from 1 to 5 volumes of the ethereal solvent, both compared with the mixture of optical isomers of formula (I) and (II).

According to an again more preferred embodiment of the invention, in the step B. the crystallization or precipitation of the compound of formula (III) is carried out by a solution of from 1.5 to 2.0 volumes of dichloromethane and, in the step C., are added from 1.5 to 2.0 volumes of the ethereal solvent, both compared with the mixture of optical isomers of formula (I) and (II).

According to an again more preferred embodiment of the invention, in the step B. the crystallization or precipitation of the compound of formula (III) is carried out from a solution of about 1.8 volumes of dichloromethane and, in the step C., are added about 1.8 volumes of the ethereal solvent, both compared with the mixture of optical isomers of formula (I) and (II).

The process of the present invention can be carried out at a temperature comprised between $-10°$ C. and $50°$ C., being preferred a range of temperature comprised between $0°$ and $25°$ C.

The step E. of the present invention consists in the isolation of Esomeprazole having increased optical purity or salts thereof from the filtrated solution of the step D.

The step E. also increases the optical purity of the product, indeed, starting from Esomeprazole in solution as prepared at the end of the step D., having typically optical purity higher than 99.7% (HPLC A/A %), isolated Esomeprazole or salt thereof having typically optical purity of 100.0% (HPLC A/A %) or about 100.0% (HPLC A/A %) are prepared.

The solution of the optically enriched Esomeprazole in a mixture of dichloromethane and ethereal solvent, as prepared in the step D, for example can be concentrated to provide isolated Esomeprazole or can be extracted with a basic aqueous solution and the latter can be converted to a Magnesium salt or sodium salt to provide respectively an Esomeprazole Magnesium salt, being preferred Esomeprazole Magnesium dihydrate or trihydrate, or to provide Esomeprazole Sodium.

With the aim to carry out the step E., the preparation of isolated Esomeprazole or Esomeprazole Magnesium dihydrate or trihydrate from an organic or aqueous solution is part of the state of the art.

The isolated Esomeprazole base or Esomeprazole Magnesium dihydrate or trihydrate or Esomeprazole sodium prepared according to the process of the present invention, and in particular, obtained at the end of the step E., have typically optical purity of 100.0% (HPLC A/A %) or about 100.0% (HPLC A/A %).

The molar yield of the process of the present invention is substantially quantitative, excepting the amount of removed impurity Omeprazole.

All the preferred embodiments said before can be combined in each combination, always providing the process of the present invention.

The starting material of the process of the present invention, i.e. a mixtures of the optical isomers of formula (I) and (II), can be prepared by asymmetric oxidation of the substrate named Ufiprazole. Said mixture, having typical ratio of 80:20 (w/w) of (S) enantiomer versus the (R) enantiomer, can be submitted to the process of the present invention which provides Esomeprazole in solution having optical purity higher than 99.7% (HPLC A/A %). Esomeprazole Magnesium dihydrate or Esomeprazole Magnesium trihydrate isolated from the solutions containing optically enriched Esomeprazole (solutions obtained at the end of step D.), have a not detected amount of (R)-Omeprazole.

EXPERIMENTAL SECTION

Enantiomerically enriched mixtures of (S)- and (R)-Omeprazole can be prepared by asymmetric oxidation of Ufiprazole according to known prior art methods.

DCM means dichloromethane; MTBE means methyl-t-buthyl ether; CPME=cyclopropylmethlyether; DIPE=Diisopropylether; AcOH=acetic acid.

Example 1: Preparation of Esomeprazole from DCM—Entry 1 of Table 1. Comparative Example—No Ethereal Solvent 392 g of an aqueous solution at pH=13.73 containing 102.89 g of Esomeprazole (prepared by asymmetric oxidation of Ufiprazole) containing 16.32% of (R)-Omeprazole (HPLC A/A %) were treated with 84 ml of 20% AcOH until pH 9.81 and then 356 mL of DCM were added. The pH was brought to 8.61 by addition of 14 ml of 20% AcOH, then the phases were separated. The aqueous phase was washed with 237 mL of DCM at 25° C. The organic phases were combined and concentrated at 25° C. under reduced pressure to 120 ml. The residue was diluted with DCM (80 ml), stirred for 1 h at 20-25° C. and filtered. The cake was washed with 2×50 mL of DCM and dried to afford 15.7 g of a white solid. The combined filtrates were diluted with 100 mL of water and taken to pH 12 by addition of 12 ml of 30% NaOH.

The organic phase was separated and washed with 50 ml of water. The combined aqueous phases contained enantiomerically enriched Esomeprazole.

The data on the product are in Entry 1 of Table 1.

Example 2: Preparation of Esomeprazole from DCM—Entry 2 of Table 1. Comparative Example—No Ethereal Solvent 392 g of an aqueous solution at pH=13.73 containing 102.89 g of Esomeprazole (prepared by asymmetric oxidation of Ufiprazole) containing 16.32% of (R)-Omeprazole (HPLC A/A %) were treated with 85 ml of 20% AcOH until pH 9.80 and then 356 mL of DCM were added. The pH was brought to 8.76 by addition of 16 ml of 20% AcOH, then the phases were separated. The aqueous phase was washed with 237 mL of DCM at 25° C. The organic phases were combined and concentrated at 20-25° C. under reduced pressure to 200 ml.

The residue was cooled to 0-5° C., stirred for 1 h and filtered. The cake was washed with 2×50 ml of DCM and dried to afford 17.2 g of a white solid. The combined filtrates were diluted with 200 mL of water and taken to pH 13 by addition of 30% NaOH.

The separated aqueous phase contained enantiomerically enriched Esomeprazole.

The data on the product are in Entry 2 of Table 1.

Example 3: Preparation of Esomeprazole from DCM+MTBE—Entry 3 of Table 1. Exemplificative of the Invention 392 g of an aqueous solution at pH=13.73 containing 102.89 g of Esomeprazole (prepared by asymmetric oxidation of Ufiprazole) containing 16.32% of (R)-Omeprazole (HPLC A/A %) were treated with 85 ml of 20% AcOH until pH 9.64 and then 356 mL of DCM were added. The pH was brought to 8.60 by addition of 17 ml of 20% AcOH, then the phases were separated. The aqueous phase was washed with 237 mL of DCM at 25° C. The organic phases were combined and concentrated at 25° C. under reduced pressure to 200 ml.

The residue was stirred for 40 min. at 25° C. (crystallization occurred) and then 200 ml of MTBE were added at 25° C. over 30 minutes. The mixture was cooled down to 0-5° C., aged for 2 h and filtered. The cake was washed with 2×50 mL of MTBE and dried to afford 36.9 g of a white solid. The combined filtrates were diluted with 200 ml of water and taken to pH 13.24 by addition of 37.5 g of 30% NaOH. The phases were separated. The aqueous phase (300 ml) contained enantiomerically enriched Esomeprazole.

The data on the product are in Entry 3 of Table 1.

Example 4: Preparation of Esomeprazole from DCM+MTBE—Entry 4 of Table 1. Exemplificative of the Invention 392 g of an aqueous solution at pH=13.73 containing 102.89 g of Esomeprazole (prepared by asymmetric oxidation of Ufiprazole) containing 16.32% of (R)-Omeprazole (HPLC A/A %) were treated with 86 ml of 20% AcOH until pH 9.55 and then 356 mL of DCM were added. The pH was brought to 8.60 by addition of 16 mL of 20% AcOH, then the phases were separated. The aqueous phase was washed with 237 mL of DCM at 25° C. The organic phases were combined and concentrated at 20-25° C. under reduced pressure to 200 ml (crystallization occurred).

200 mL of MTBE were then added to the residue (a suspension) at 25° C. over 30 minutes. The mixture was cooled down to 0-5° C., aged for 2 h and filtered. The cake was washed with 2×50 mL of MTBE at 0° C. and dried to afford 37.7 g of a white solid. The combined filtrates were diluted with 200 ml of water and taken to pH 13.23 by addition of 37.9 g of 30% NaOH. The phases were separated. The aqueous phase (310 ml) contained enantiomerically enriched Esomeprazole.

The data on the product are in Entry 4 of Table 1.

Example 5: Preparation of Esomeprazole from DCM+MTBE—Entry 5 of Table 1. Exemplificative of the Invention 392 g of a different aqueous solution at pH=13.60 containing 111.58 g of Esomeprazole (prepared by asymmetric oxidation of Ufiprazole) containing 19.16% of (R)-Omeprazole (HPLC A/A %) were treated with 82 ml of 20% AcOH until pH 9.60 and then 356 mL of DCM were added. The pH was brought to 8.60 by addition of 13 ml of 20% AcOH, then the phases were separated. The aqueous phase was washed with 237 mL of DCM at 25° C. The organic phases were combined and concentrated at 20-25° C. under reduced pressure to 200 ml (crystallization occurred).

To the residue (a suspension) were then added 200 mL of MTBE at 25° C. over 30 minutes. The mixture was cooled down to 0-5° C., aged for 2 h and filtered. The cake was washed with 2×50 mL of MTBE at 0° C. and dried to afford 40.5 g of a white solid. The combined filtrates were diluted with 200 ml of water and taken to pH 13.26 by addition of 37.2 g of 30% NaOH. The phases were separated. The aqueous phase (300 ml) contained enantiomerically enriched Esomeprazole.

The data on the product are in Entry 5 of Table 1.

Example 6: Preparation of Esomeprazole from DCM+MTBE—Entry 6 of Table 1. Exemplificative of the Invention 784 g of an aqueous solution at pH=13.72 containing 223.16 g of Esomeprazole (prepared by asymmetric oxidation of Ufiprazole) containing 19.16% of (R)-Omeprazole (HPLC A/A %) were treated with 176 ml of 20% AcOH until pH 9.69 and then 712 mL of DCM were added. The pH was brought to 8.70 by addition of 32 ml of 20% AcOH, then the phases were separated. The aqueous phase was washed with 474 mL of DCM at 25° C. The organic phases were combined and concentrated at 20-25° C. under reduced pressure to 400 ml (crystallization occurred).

The residue (a suspension) was then added with 400 mL of MTBE at 25° C. over 30 minutes. The mixture was cooled down to 0-5° C., aged for 2 h and filtered. The cake was washed with 2×100 mL of MTBE at 0° C. and dried to afford 84.1 g of a white solid. The combined filtrates were diluted with 400 ml of water and taken to pH 13.28 by addition of 70.7 g of 30% NaOH. The phases were separated. The aqueous phase (605 ml) contained enantiomerically enriched Esomeprazole.

The data on the product are in Entry 6 of Table 1.

Example 7: Preparation of Esomeprazole from DCM+MTBE—Entry 7 of Table 1. Exemplificative of the Invention 784 g of a different aqueous solution at pH=13.46 containing 217.58 g of Esomeprazole (prepared by asymmetric oxidation of Ufiprazole) containing 22.48% of (R)-Omeprazole (HPLC A/A %) were treated with 170 ml of 20% AcOH until pH 9.80 and then 712 mL of DCM were added. The pH was brought to 8.75 by addition of 47 ml of 20% AcOH, then the phases were separated. The aqueous phase was washed with 474 mL of DCM at 25° C. The organic phases were combined and concentrated at 20-25° C. under reduced pressure to 400 ml.

The residue was stirred for 10 min. (crystallization occurred) and then 400 mL of MTBE at 25° C. over 30 minutes were added to the suspension. The mixture was cooled down to 0-5° C., aged for 2 h and filtered. The cake was washed with 2×100 mL of MTBE at 0° C. and dried to afford 99.3 g of a white solid. The combined filtrates were diluted with 400 ml of water and taken to pH 13.3 by addition of 90.5 g of 30% NaOH. The phases were separated. The aqueous phase (590 ml) contained enantiomerically enriched Esomeprazole.

The data on the product are in Entry 7 of Table 1.

Example 8: Preparation of Esomeprazole from DCM+MTBE—Entry 8 of Table 1. Exemplificative of the Invention 392 g of a different aqueous solution at pH=13.60 containing 111.58 g of Esomeprazole (prepared by asymmetric oxidation of Ufiprazole) containing 19.16% of (R)-Omeprazole (HPLC A/A %) were treated with 85 ml of 20% AcOH until pH 9.70 and then 356 mL of DCM were added. The pH was brought to 8.60 by addition of 22 ml of 20% AcOH, then the phases were separated. The aqueous phase was washed with 237 mL of DCM at 25° C. The organic phases were combined and concentrated at 20-25° C. under reduced pressure to 200 ml.

The residue was stirred for 10 min and then, to promote the crystallization, the solution was seeded with Omperazole. After the seeding crystallization occurred and then the suspension was added with 200 of MTBE at 25° C. over 30 minutes. The mixture was cooled down to 0-5° C., aged for 2 h and filtered. The cake was washed with 2×50 mL of MTBE and dried to afford 42.6 g of a white solid. The combined filtrates were diluted with 200 ml of water and taken to pH>13 by addition of 36 g of 30% NaOH. The phases were separated. The aqueous phase (299 ml) contained enantiomerically enriched Esomeprazole.

The data on the product are in Entry 8 of Table 1.

Example 9: Preparation of Esomeprazole from DCM+MTBE—Entry 9 of Table 1. Exemplificative of the Invention 392 g of a different aqueous solution at pH=13.60 containing 108.79 g of Esomeprazole (prepared by asymmetric oxidation of Ufiprazole) containing 22.48% of (R)-Omeprazole (HPLC A/A %) were treated with 85 ml of 20% AcOH until pH 9.90 and then 356 mL of DCM were added. The pH was brought to 8.83 by addition of 17 ml of 20% AcOH, then the phases were separated. The aqueous phase was washed with 237 mL of DCM at 25° C. The organic phases were combined and concentrated at 30° C. under reduced pressure to 200 ml.

The residue was stirred at 25° C. for 15 minutes (crystallization occurred) and then the suspension was added with 200 ml of MTBE at 25° C. over 30 minutes. The mixture was cooled down to 0-5° C., aged for 2 h and filtered. The cake was washed with 2×50 mL of MTBE and dried to afford 51.9 g of a white solid. The combined filtrates were diluted with 200 ml of water and taken to pH 13.08 by addition of 28.3 g. of 30% NaOH. The phases were separated. The aqueous phase (285 ml) contained enantiomerically enriched Esomeprazole.

The data on the product are in Entry 9 of Table 1.

Example 10: Preparation of Esomeprazole from DCM+DIPE—Entry 10 of Table 1. Exemplificative of the Invention, with Diisopropylether 392 g of a aqueous solution at pH=13.60 containing 108.79 g of Esomeprazole (prepared by asymmetric oxidation of Ufiprazole) containing 22.48% of (R)-Omeprazole (HPLC A/A %) were treated with 85 ml of 20% AcOH until pH 9.86 and then 356 mL of DCM were added. The pH was brought to 8.81 by addition of 18 ml of 20% AcOH, then the phases were separated. The aqueous phase was washed with 237 mL of DCM at 25° C. The organic phases were combined and concentrated at 20-25° C. under reduced pressure to 200 ml.

The residue was stirred at 25° C. for 15 minutes (crystallization occurred) and then the suspension was added with 200 mL of diisopropylether (DIPE) at 25° C. over 30 minutes. The mixture was cooled down to 0-5° C., aged for 2 h and filtered. The cake was washed with 2×50 mL of DIPE and dried to afford 49.9 g of a white solid. The combined filtrates were diluted with 200 ml of water and taken to pH 13.2 by addition of 29.3 g of 30% NaOH. The phases were separated. The aqueous phase (285 ml) contained enantiomerically enriched Esomeprazole.

The data on the product are in Entry 10 of Table 1.

Example 11: Table of Comparison Showing the Effect of the Invention

TABLE 1

| Exp. | Starting material | | Product in phase at the end of step D. | | Removed Omeprazole | |
|---|---|---|---|---|---|---|
| | Eso (g) | R (%) | Eso (g) | R (%) | Ome (g) | R (%) |
| 1 | 102.89 | 16.32 | 86.97 | 10.60 | 15.7 | 49.50 |
| 2 | 102.89 | 16.32 | 86.96 | 9.74 | 17.2 | 49.11 |
| 3 | 102.89 | 16.32 | 70.67 | 0.15 | 36.9 | 48.51 |
| 4 | 102.89 | 16.32 | 69.62 | 0.21 | 37.7 | 48.74 |

TABLE 1-continued

| | Starting material | | Product in phase at the end of step D. | | Removed Omeprazole | |
|---|---|---|---|---|---|---|
| Exp. | Eso (g) | R (%) | Eso (g) | R (%) | Ome (g) | R (%) |
| 5 | 111.58 | 19.16 | 62.39 | 0.17 | 40.5 | 49.24 |
| 6 | 223.16 | 19.16 | 105.93 | 0.15 | 84.1 | 49.21 |
| 7 | 217.58 | 22.48 | 113.30 | 0.28 | 99.3 | 49.29 |
| 8 | 111.58 | 19.16 | 56.73 | 0.16 | 42.6 | N/A |
| 9 | 108.79 | 22.48 | 50.81 | 0.17 | 51.9 | 47.98 |
| 10 | 108.79 | 22.48 | 49.90 | 0.22 | 49.9 | 48.00 |

The percentage values for (R) isomer, i.e. (R)-Omperazole of the Table 1 are expressed as percentage in percentual area (HPLC A/A %) and are determinated using the HPLC method of example 13. Eso means Esomperazole or mixtures of isomers of formula (I) and (II).

In the Table 1, the weight of Esomeprazole present in the starting solution and the weight present in the phase at the end of the step D. were determined by HPLC assay, therefore said weight values are affected by an estimated error of about 10%.

By comparison of entries 1-2 with the other entries 3-10, it is possible to see the clear effect of the process of the present invention, indeed the content of (R)-Omeprazole in Esomeprazole drops to values lower than 0.30% in the experiments wherein the addition of the ethereal solvent has been carried out.

As reported in table 1, efficient removal of the R enantiomer could be achieved only by addition of the ethereal solvent.

Example 12: General Procedure for the Preparation of Esomeprazole Having High Optical Purity To an aqueous solution of S and R enantiomers of Omeprazole (784 g) was added a 20% solution of acetic acid in water at 20-25° C. to take the pH to 9.5-10.0. The resulting mixture was diluted with dichloromethane (712 mL) and the pH of the mixture was taken to 8.5-9.0 by addition of 20% solution of acetic acid in water. The separated aqueous phase was extracted with dichloromethane (474 mL) and the two combined phases were concentrated to a residue of 400 mL. The residue was stirred at 20-25° C. and TBME (400 mL) was added in 30 min. The resulting mixture was cooled to 0-5° C., aged for 2 h and filtered. The wet cake was washed with TBME (2×100 mL) and the solid was dried at 25-30° C. The isolated solid contained a racemic mixture of the product.

The combined mother liquors and cake washings contained pure Esomeprazole and were extracted with basic water (pH>13) and stored in aqueous solution for the known instability at low pH.

Pure Esomeprazole can be conveniently used to prepare Esomeprazole magnesium or sodium salts.

Example 13: Analytical Method for the Determination of the Chiral Purity by HPLC of the Mixtures of the Optical Isomers of Formula (I) and (II)

Cromatographic Conditions:
Column: Chiral-AGP, 100×4.0 mm, 5 μm or equivalent.
Column Temp.: Ambient (25° C.)
Mobile phase: Phosphate buffer at pH=6/Acetonitrile 425:75 (v/v)
Flow: 0.6 mL/min
Detector: UV at 302 nm, bw 4 nm
Injection volume: 20 μL
Diluent: Buffer at pH 11
Analysis time: 30 min.
Note: samples have to be analyzed immediately and stored/transported in an ice bath.
The retention times are as follows:
Compound RT(min) RRT
(R)-Omeprazole 3.5 0.8
Esomprazole 4.6 1.0

The invention claimed is:
1. Process for the preparation of Esomeprazole having high optical purity of formula (I):

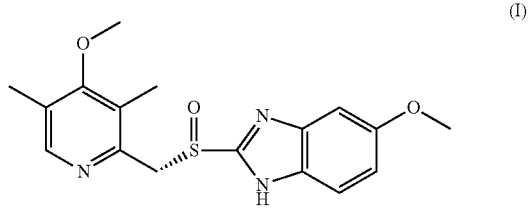

comprising the following steps:
A. providing a solution containing an enantiomerically enriched mixture of the optical isomers of formula (I) and (II):

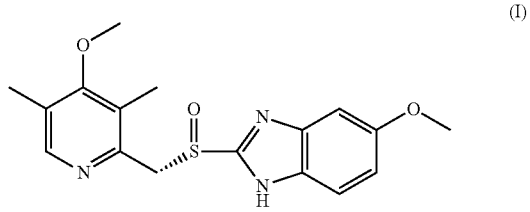

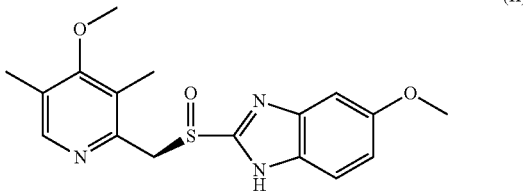

wherein the ratio between the optical isomers (I) and (II) is from 60:40 to 99:1, and wherein the solvent of said solution is dichloromethane;
B. promoting the crystallization of the compound of formula (III):

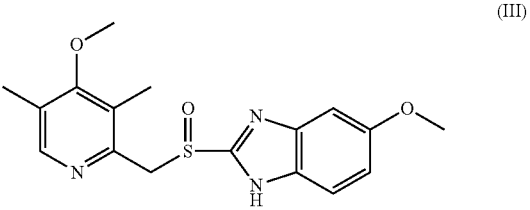

said compound being substantially in racemic form;

C. adding an ethereal solvent to the suspension prepared in the step B;

D. filtering the suspension prepared in the step C to remove the compound of formula (III);

E. isolating Esomeprazole having increased optical purity or salts thereof from the filtrated solution of the step D.

2. Process according the to claim 1 wherein the amount of dichloromethane for step A. ranges from 1 to 5 volumes compared with the mixture of optical isomers of formula (I) and (II).

3. Process according to claim 1 wherein step B. is carried out by concentration of the dichloromethane solution of the step A., from a range from 20 to 3 volumes to a range from 5 to 1 volumes compared with the mixture of optical isomers (I) and (II).

4. Process according to claim 3 wherein step B. is carried out by concentration of the dichloromethane solution of step A., from a range from 6 to 4 volumes to a range from 2.0 to 1.5 volumes compared with the mixture of optical isomers (I) and (II).

5. Process according to claim 1 wherein the ethereal solvent is chosen from the group consisting of methyl-t-buthylether, diisopropylether, dibuthylether and cyclopentyl methyl ether.

6. Process according to claim 5 wherein the ethereal solvent is methyl-t-buthylether.

7. Process according to claim 1 wherein in step C. the amount of added ethereal solvent is between 1 to 5 volumes compared with the mixture of optical isomers of formula (I) and (II).

8. Process according to claim 7 wherein in step C. the amount of added ethereal solvent is between 1.5 to 2.0 volumes compared with the mixture of optical isomers of formula (I) and (II).

9. Process according to claim 1 wherein in step C. the addition of the ethereal solvent is performed in a time between 20 and 40 minutes.

10. Process according to claim 1 wherein in step B. the crystallization of the compound of formula (III) is carried out from a solution of from 1 to 5 volumes of dichloromethane and, in step C., are added from 1 to 5 volumes of the ethereal solvent, both compared with the mixture of optical isomers of formula (I) and (II).

11. Process according to claim 10 wherein in step B. the crystallization of the compound of formula (III) is carried out from a solution of from 1.5 to 2.0 volumes of dichloromethane and, in step C., are added from 1.5 to 2.0 volumes of the ethereal solvent, both compared with the mixture of optical isomers of formula (I) and (II).

12. Process according to claim 1 wherein all the steps are carried out at a temperature between 0° C. and 25° C.

13. Process according to claim 1 wherein, at the end of step D., Esomeprazole has optical purity higher than 99.7% (HPLC A/A %).

14. Process according to claim 1 wherein in step E. Esomeprazole is isolated as Esomeprazole or Esomeprazole Magnesium dihydrate or trihydrate or Esomeprazole Sodium.

15. Process according to claim 1 wherein at the end of step E. the isolated Esomeprazole or Esomeprazole Magnesium dihydrate or trihydrate or Esomeprazole Sodium has optical purity of 100.0% (HPLC A/A %).

* * * * *